(12) United States Patent
Russo

(10) Patent No.: US 11,726,054 B2
(45) Date of Patent: Aug. 15, 2023

(54) NFC-ENABLED TEST SENSORS, SYSTEMS AND METHODS USING THE SAME

(71) Applicant: Ascensia Diabetes Care Holdings AG, Basel (CH)

(72) Inventor: Anthony P. Russo, New York, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 247 days.

(21) Appl. No.: 17/102,815

(22) Filed: Nov. 24, 2020

(65) Prior Publication Data
US 2022/0163477 A1    May 26, 2022

(51) Int. Cl.
  *G01N 27/327* (2006.01)
(52) U.S. Cl.
  CPC ..... *G01N 27/3273* (2013.01); *G01N 27/3272* (2013.01)
(58) Field of Classification Search
  None
  See application file for complete search history.

(56) References Cited

U.S. PATENT DOCUMENTS

| | | | |
|---|---|---|---|
| 2007/0270672 A1 | 11/2007 | Hayter | |
| 2010/0012509 A1 | 1/2010 | Brenneman et al. | |
| 2014/0318987 A1* | 10/2014 | Guthrie | G01N 27/3273 205/782 |
| 2015/0083796 A1* | 3/2015 | Kyung | G06K 19/0716 235/375 |
| 2015/0130628 A1 | 5/2015 | Kyung et al. | |
| 2018/0153450 A1 | 6/2018 | Routh et al. | |
| 2020/0155047 A1 | 5/2020 | Rogers et al. | |
| 2020/0365240 A1 | 11/2020 | Chen et al. | |

OTHER PUBLICATIONS

WIPO Patent Application No. PCT/IB2021/060837, International Search Report and Written Opinion of the International Searching Authority, dated Feb. 23, 2022.

* cited by examiner

*Primary Examiner* — J. Christopher Ball
(74) *Attorney, Agent, or Firm* — Erise IP, P.A.

(57) ABSTRACT

An electrochemical test sensor is adapted to receive a fluid sample including an analyte. The electrochemical test sensor includes a base. The base includes an enzyme adapted to react with the analyte. The electrochemical test sensor further includes a plurality of electrodes, a near field communication (NFC) tag chip, an analog front end (AFE) and a microcontroller.

28 Claims, 7 Drawing Sheets

NFC-ENABLED TEST SENSORS, SYSTEMS AND METHODS USING THE SAME

FIELD OF THE INVENTION

The present invention relates generally to an electrochemical test sensor for determining an analyte concentration. More specifically, the present invention generally relates to an electrochemical test sensor, systems and methods for determining an analyte concentration in the absence of an analyte meter.

BACKGROUND OF THE INVENTION

The quantitative determination of analytes in body fluids is of great importance in the diagnoses and maintenance of certain physical conditions. For example, lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a fluid sample of blood.

In a typical scenario, to determine an analyte concentration, a user would carry a plurality of test sensors (e.g., electrochemical test sensors) and an analyte meter (e.g., a blood glucose meter). An analyte meter typically includes an opening to receive a test sensor, a memory, a processor, a display for showing the testing results, and a plurality of buttons or other mechanisms to navigate the display. The analyte meter may require some user setup and a learning curve associated with it. Some of the analyte meters may require pairing with a smartphone using a wireless technology such as BLUETOOTH®.

It would be desirable to streamline such an approach to provide maximum user convenience, while still providing desired features of a typical analyte-determining system.

SUMMARY

According to one embodiment, an electrochemical test sensor is adapted to receive a fluid sample including an analyte. The electrochemical test sensor includes a base. The base includes an enzyme adapted to react with the analyte. The electrochemical test sensor further includes a plurality of electrodes, a near field communication (NFC) tag chip, an analog front end (AFE) and a microcontroller.

According to another embodiment, a system is adapted to determine an analyte information of a fluid sample. The system includes an electrochemical test sensor and an NFC-enabled reader. The electrochemical test sensor is adapted to receive the fluid sample of an analyte. The electrochemical test sensor includes a base. The base includes an enzyme adapted to react with the analyte. The electrochemical test sensor further includes a plurality of electrodes, a near field communication (NFC) tag chip, an analog front end (AFE) and a microcontroller. The NFC-enabled reader is configured to wirelessly receive data from the electrochemical test sensor to assist in determining the analyte information of the fluid sample.

According to one method, analyte information of a fluid sample is determined. The method includes providing an electrochemical test sensor adapted to receive the fluid sample of an analyte. The electrochemical test sensor includes a base. The base includes an enzyme adapted to react with the analyte. The electrochemical test sensor further includes a plurality of electrodes, a near field communication (NFC) tag chip, an analog front end (AFE) and a microcontroller. The fluid sample is contacted with the electrochemical test sensor. The electrochemical test sensor is brought in close proximity to an NFC-enabled reader. After bringing the electrochemical test sensor in close proximity to the NFC-enabled reader, the near field communication (NFC) tag chip and the analog front end (AFE) are powered. The analog front end assists in starting an electrochemical reaction with the analyte of the fluid sample. Data is wirelessly transmitted from the electrochemical reaction via the NFC tag chip of the electrochemical test sensor to the NFC-enabled reader. Analyte information of the fluid sample is determined on the NFC-enabled reader using the data received from the electrochemical test sensor.

The above summary is not intended to represent each embodiment or every aspect of the present invention. Additional features and benefits of the present invention are apparent from the detailed description and figures set forth below.

BRIEF DESCRIPTION OF THE DRAWINGS

Other advantages of the invention will become apparent upon reading the following detailed description and upon reference to the drawings in which.

Figure 1A:
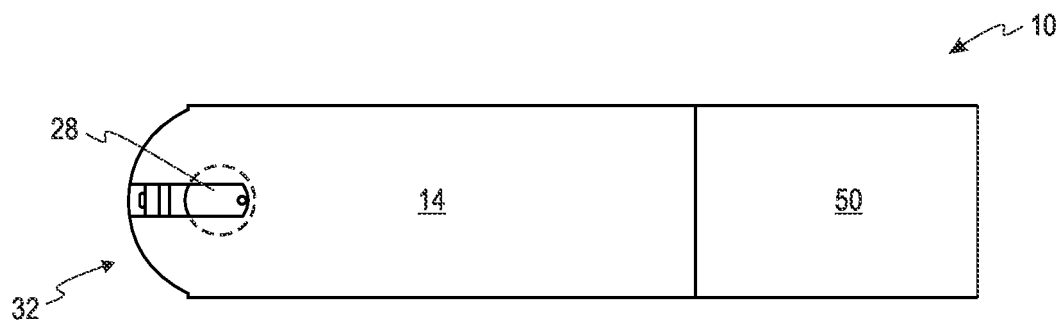
FIG. 1A is a top view of an electrochemical test sensor according to one embodiment.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The electrochemical test sensors are adapted to receive a fluid sample. The test sensor assists in determining information related to analytes such as analyte concentrations. As used within this application, the term "concentration" refers to an analyte concentration, activity (e.g., enzymes and electrolytes), titers (e.g., antibodies), or any other measure concentration used to measure the desired analyte. Analytes that may be measured include glucose, lipid profiles (e.g., cholesterol, triglycerides, LDL and HDL), microalbumin, hemoglobin A1C, urea, creatinine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

In one embodiment, an electrochemical test sensor is adapted to receive a fluid sample including an analyte. The electrochemical test sensor comprises a base. The base includes an enzyme adapted to react with the analyte. The electrochemical test sensor further including a plurality of electrodes, a near field communication (NFC) tag chip, an analog front end (AFE) and a microcontroller.

The present invention is advantageous in that the electrochemical test sensors function in the absence of an analyte meter (e.g., a glucose meter). Thus, an analyte meter is not used with the electrochemical test sensor of the present invention. Here, a user conveniently avoids needing to carry an analyte meter for determining analyte concentrations. Furthermore, unlike with using traditional analyte meters, there is little to no set-up and learning curve involved with the methods of the present invention.

The present invention is also advantageous in its ability to more easily modify the algorithms for calculating the analyte concentrations. In the present invention, the algorithm may be part of an NFC-enabled reader (e.g., a smartphone) in an application or could exist in, for example, a server farm in the cloud. It is convenient and significantly easy to update the algorithm in the present invention for the users and, thus, updates can be more frequent, if desired. This is in contrast to modifying algorithms stored in firmware in an analyte meter that would need to support, for example, in an over-an-air update or replacing the entire analyte meter. This would also not only be much more difficult to update, but costly as well, especially if the analyte meter needed to be replaced.

There may be other advantages to the electrochemical test sensors of the present invention. For example, a situation could arise in an emergency care setting (e.g., a hospital) or with an emergency medical technician (EMT) in which the present invention could assist in making easier and quicker decisions. For example, the electrochemical test sensors of the present invention may be used in many locations in conjunction with an NFC-enabled reader without the need for a traditional analyte meter nearby, leading to potential speed and convenience.

The test sensors described herein are electrochemical test sensors. One non-limiting example of an electrochemical test sensor is shown in FIGS. 1A-1D. FIGS. 1A-1D depict an electrochemical test sensor 10 including a base 12, a lid 14, a fluid-receiving area or channel 16, and a plurality of electrodes 18, 20, 22 and 24. The fluid-receiving area 16 in one embodiment is a capillary channel. The plurality of electrodes includes a counter electrode 18, a working (measuring) electrode 20, a detection fill electrode 22 and a hematocrit electrode 24. The fluid-receiving area 16 provides a flow path for introducing the fluid sample into the electrochemical test sensor 10. The electrodes 18, 20, 22 and 24 are coupled to a respective one of a plurality of conductive leads 26a, 26b, 26c and 26d that communicates with a near field communication (NFC) tag chip 50. The plurality of electrodes may be made from a variety of conductive materials including, but not limited to, gold, platinum, rhodium, palladium, ruthenium, carbon or combinations thereof.

It is contemplated that less than four electrodes may be used in other embodiments. For example, in one embodiment, an electrochemical test sensor may include two electrodes (a working electrode and a counter electrode). In another embodiment, an electrochemical test sensor may include three electrodes (a working electrode, a counter electrode and a detection fill electrode). It is contemplated that other electrodes may be used in the electrochemical test sensors.

The reagent area 28 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically includes an analyte-specific enzyme that reacts with the analyte and with an electron acceptor to produce an electrochemically measurable species that may be detected by the electrodes. If the analyte is glucose, the reagent would include an enzyme such as glucose oxidase or glucose dehydrogenase.

The reagent typically includes a mediator that assists in transferring electrons between the analyte and the electrodes. Non-limiting examples of mediators include phenoxazines, phenothizaines, ferricyanide or a tetrazolium salt among others familiar to those skilled in the art. The reagent may include binders that hold the enzyme and mediator together, buffers, cellulose polymers, surfactants, other inert ingredients, or combinations thereof.

A fluid sample (e.g., blood) is applied to the reagent area 28 via the fluid-receiving area 16 in one embodiment. The fluid sample reacts with the at least one reagent. After reacting with the reagent and in conjunction with the plurality of electrodes, the fluid sample produces electrical signals that will assist in determining the analyte concentration. The conductive leads 26a-26d carry the electrical signals back toward an analog front end (AFE) 52 of the NFC tag chip 50 as will be discussed below.

Figure 1B:
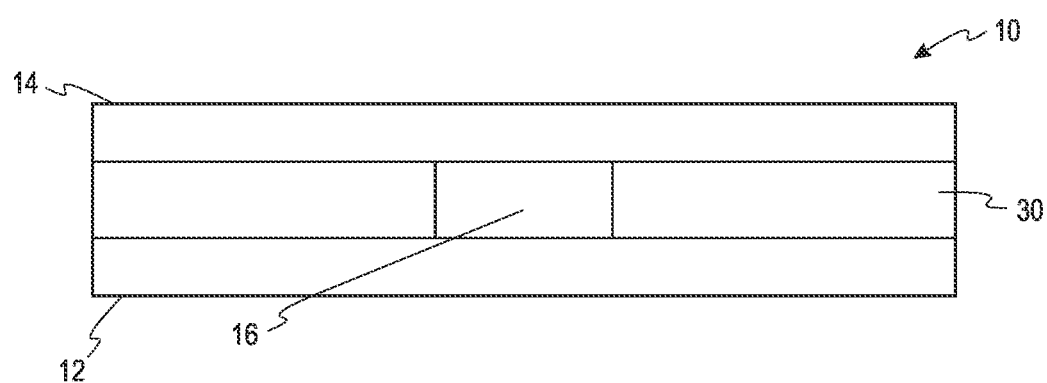
FIG. 1B is a front view of the electrochemical test sensor of FIG. 1A.
Figure 1C:
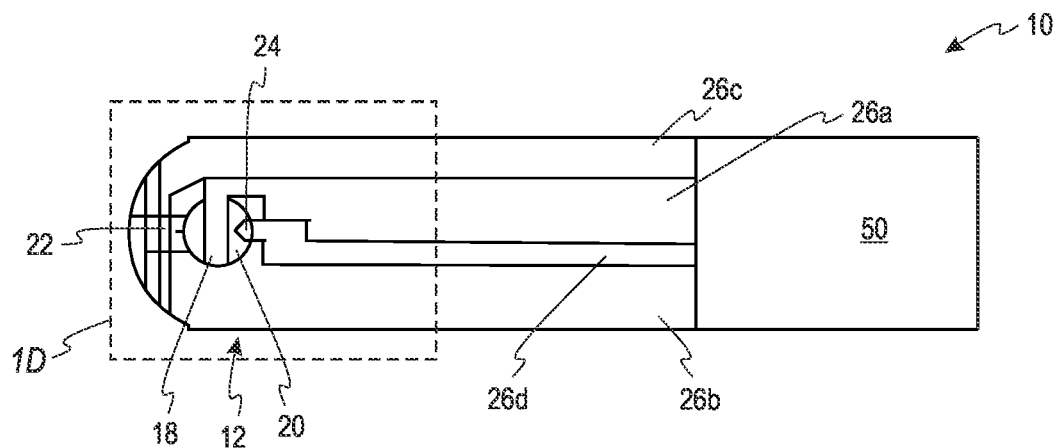
FIG. 1C is a top view of the electrochemical test sensor of FIG. 1A after the lid and the spacer have been removed.
Figure 1D:
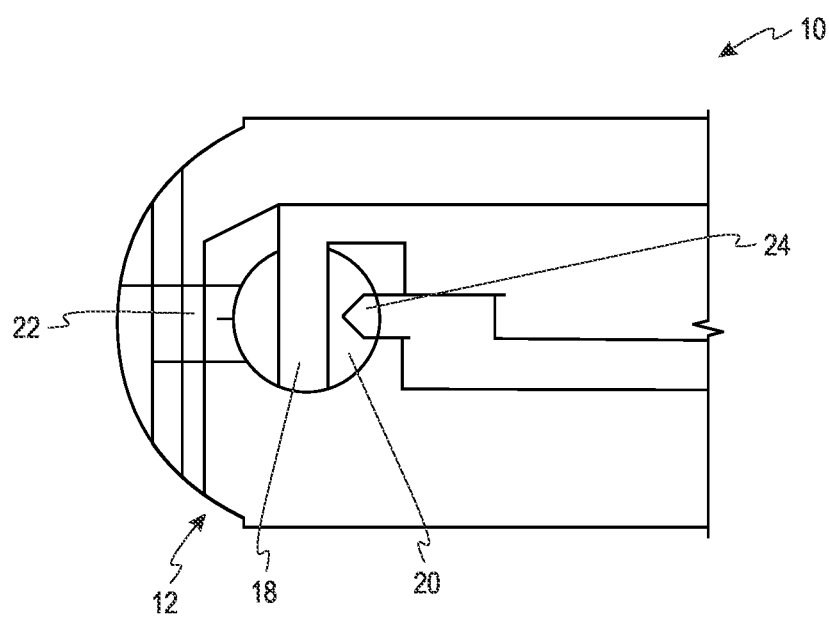
FIG. 1D is an enlarged view of generally rectangular area 1D shown in FIG. 1C.

Referring to FIG. 1B, a front view of the electrochemical test sensor 10 of FIG. 1A is shown. As shown in FIG. 1B, the electrochemical test sensor 10 includes the lid 14, a spacer 30 and the base 12. The combination of the lid 14, the spacer 30 and the base 12 forms the fluid-receiving area 16. The base 12, the lid 14 and the spacer 30 may be made from a variety of materials such as polymeric materials. Non-limiting examples of polymeric materials that may be used to form the base 12, the lid 14, and the spacer 30 include polycarbonate, polyethylene terephthalate (PET), polyethylene naphthalate (PEN), polyimide, and combinations thereof. It is contemplated that the base, spacer and lid may be independently made of other materials. It is contemplated that other materials may be used in forming the base 12, lid 14, and/or spacer 30.

To form the electrochemical test sensor 10 of FIGS. 1A-1D, the base 12, the spacer 30, and the lid 14 are attached by, for example, an adhesive or heat sealing. When the base 12, the lid 14, and the spacer 30 are attached, the fluid-receiving area 16 is formed. As shown in FIG. 1A, the fluid-receiving area 16 is formed at a first end or testing end 32 of the electrochemical test sensor 10.

It is also contemplated that the electrochemical test sensor may be formed in the absence of a spacer. For example, the electrochemical test sensor may include a base and a lid such that a fluid-receiving area (e.g., a capillary channel) is formed when the base and the lid are attached to each other. It is contemplated that the electrochemical test sensor may be formed only using the base.

Figure 2A:
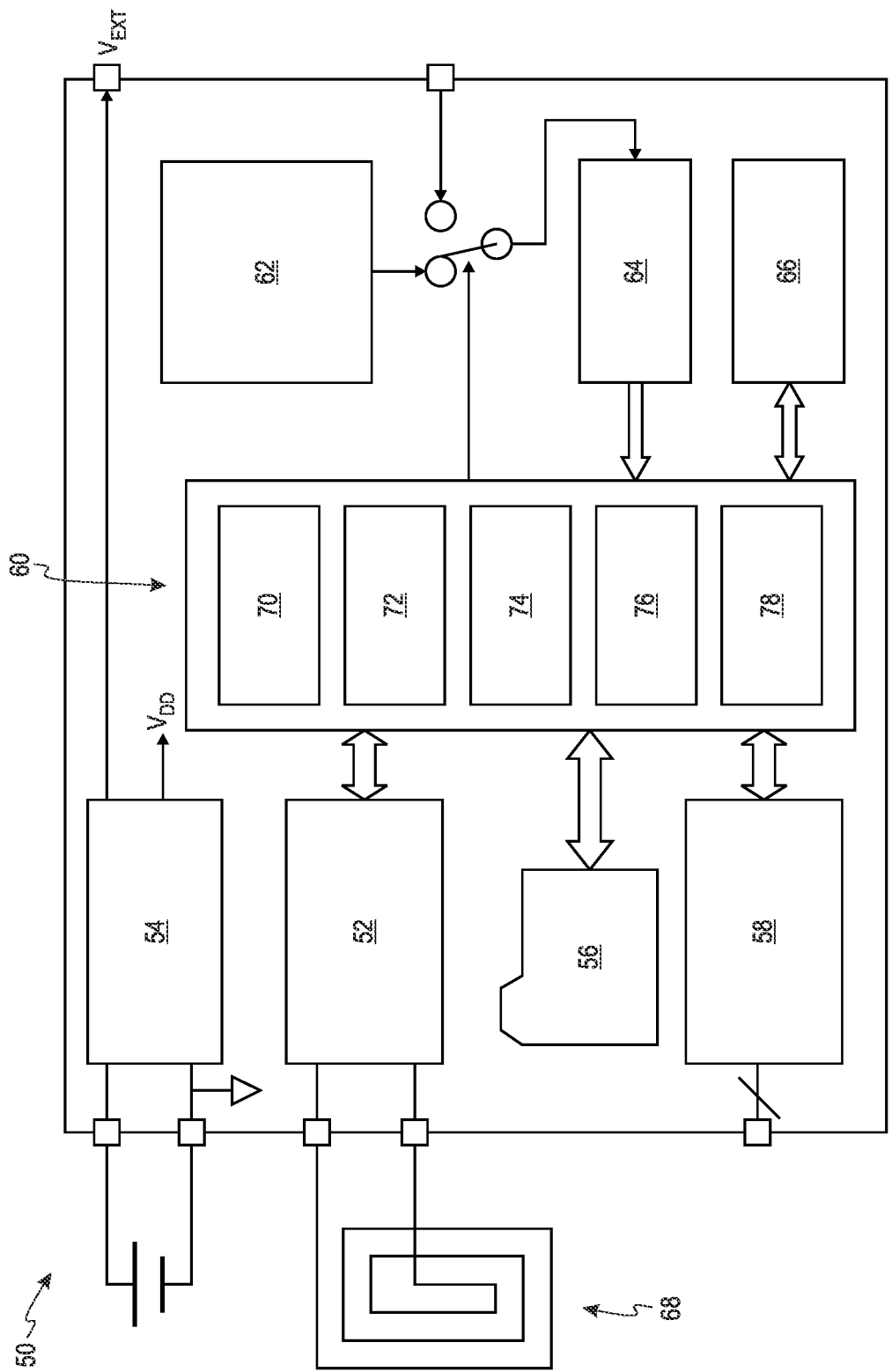
FIG. 2A is a schematic of the near field communication (NFC) tag chip shown in FIGS. 1A and 1C.

Referring to FIGS. 1A and 2A, the electrochemical test sensor includes the near field communication (NFC) tag chip 50. The NFC tag chip 50 may be secured to the electrochemical test sensor 10 by, for example, suitable adhesives and/or a mechanical coupling mechanism such as prongs. It is contemplated that other methods may be used in securing the NFC tag chip to the electrochemical test sensor.

Near field communication (NFC) includes a small antenna and hardware to communicate via the NFC standard. Near field communication (NFC) is a known worldwide standard that provides wireless data connectivity at a close proximity. NFC is currently used for communication distances of about 20 cm or less, and more likely about 10 cm or less. In other embodiments, NFC is typically used in communication distances of less than about 8 cm or less than 6 cm. In another embodiment, NFC is more commonly used in communication distances of less than about 5 or about less than about 4 cm. The NFC tag chip of the electrochemical test sensor wirelessly communicates with the NFC-enabled reader when in close proximity.

Near field communication (NFC) allows for simplified transactions, data exchange, and connections with a touch. Formed in 2004, the Near Field Communication Forum (NFC Forum) promotes sharing, pairing, and transactions between NFC-enabled readers or devices, and develops and certifies device compliance with NFC standards. NFC operates at 13.56 MHz on ISO/IEC 18000-3 air interface and at rates ranging from 106 kbit/s to 848 kbit/s. NFC's short range helps keep encrypted information private. Thus, an NFC-enabled reader such as, for example, a smartphone, tablet, computer or kiosk can receive information from the electrochemical test sensor to assist in determining an analyte concentration.

Referring specifically to FIG. 2A, the near field communication (NFC) tag chip 50 includes the analog front end (AFE) 52, a power management module 54, memory 56, a serial periphery interface (SPI slave) 58, a microcontroller 60, an on-chip temperature sensor 62, an analog/digital (A/D) converter 64, a real-time clock 66 and an antenna 68. The microcontroller 60 also includes a control or processing logic module 70, a memory interface 72, a cryptographic module 74, an authentication module 76, and an anti-collision module 78. It is noted that all NFC tag chips do not include all of these modules or features. For example, some NFC tag chips do not include temperature sensors.

In this embodiment, the NFC tag chip 50 does not include a battery. In this embodiment, the near field communication (NFC) tag chip 50 has the ability to receive power from an NFC-enabled reader. Thus, the NFC tag chip is fully passive. The NFC tag chip in this embodiment involves an initiator (an NFC-enabled reader) and a target (the electrochemical test sensor with NFC tag chip). The initiator actively generates an RF field that powers a passive target. This enables NFC targets to take very simple form factors such as tags or stickers that do not require batteries.

Figure 2B:
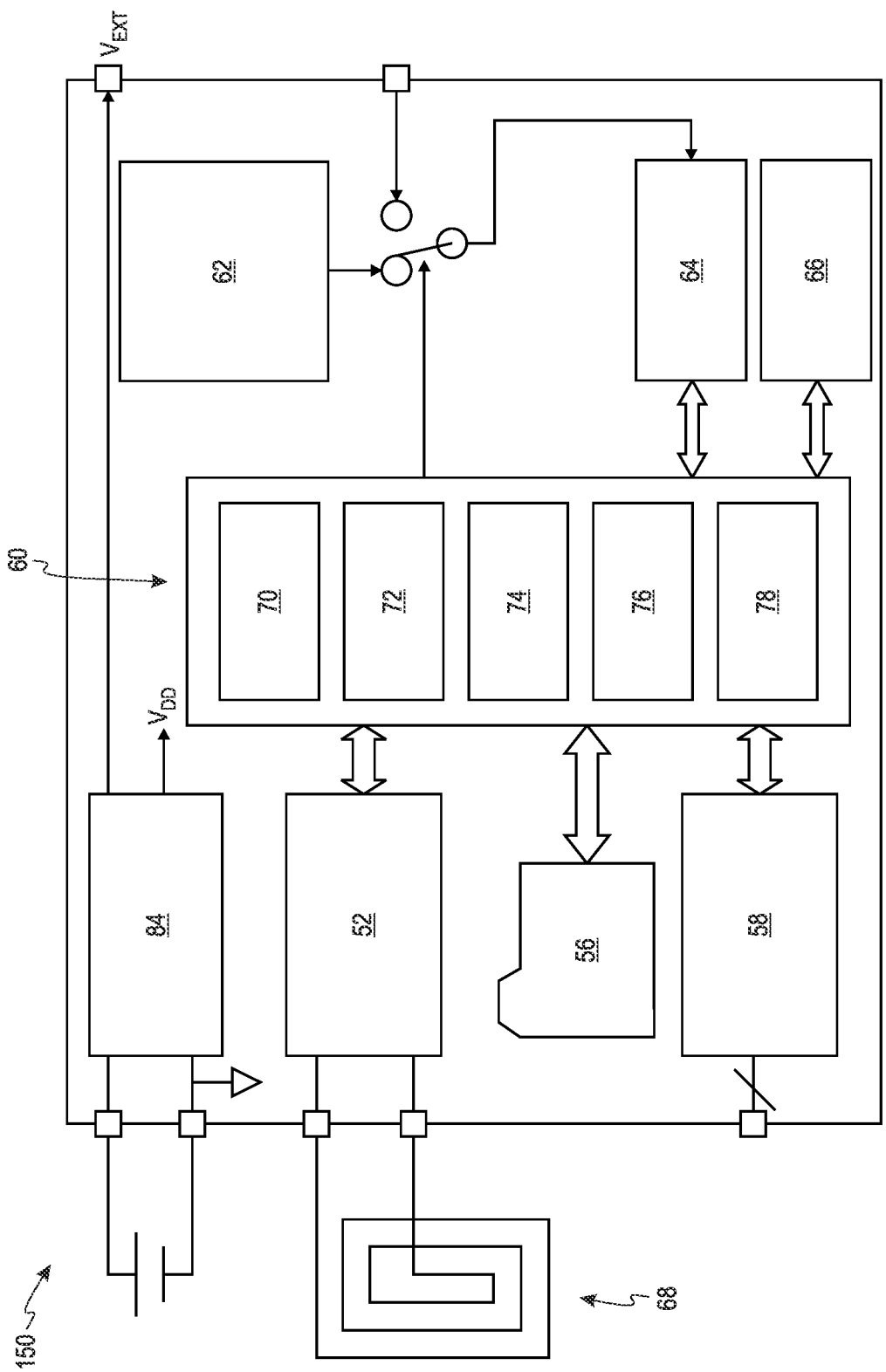
FIG. 2B is a schematic of the near field communication (NFC) tag chip according to another embodiment.
Figure 3:
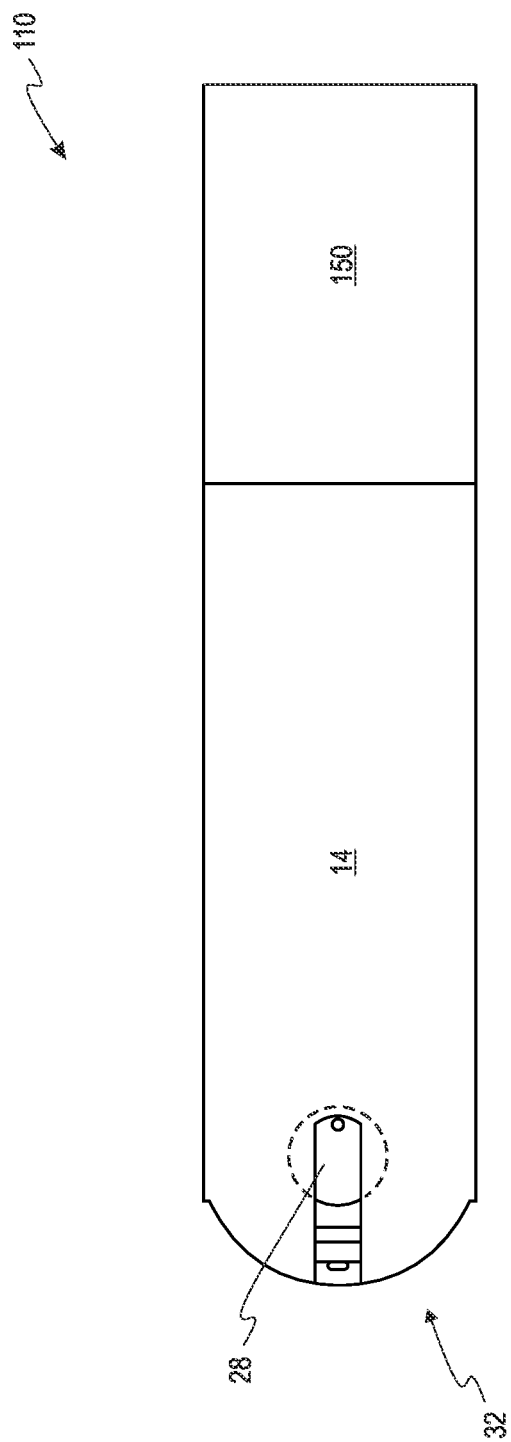
FIG. 3 is a top view of an electrochemical test sensor according to another embodiment.

In another embodiment, an NFC-enabled dongle may include a battery to power the near field communication (NFC) and/or the AFE module for signal sampling. Referring to FIG. 2B, an NFC tag chip 150 includes a battery 84. The NFC tag chip 150 includes all of the modules as described in the NFC tag chip 50 except for the power management module 54, which is not needed when the battery 84 is included. The NFC tag chip 150 is used in an electrochemical test sensor according to another embodiment. In one embodiment, the battery 84 is a 1.5 or 3V battery used to power the NFC tag chip 150. NFC peer-to-peer communication is of course possible where both devices are powered. For example, an electrochemical test sensor 110 with a battery 84 in the NFC tag chip 150 may be configured to implement a peer-to peer communication with an NFC-enabled reader.

A non-limiting commercial example of a near field communication (NFC) tag chip, which includes a microcontroller and an analog front end (AFE), that may be used in the present invention is SL13A-AQFM manufactured/marketed by Ams.

A non-limiting commercial example of a near field communication (NFC) tag chip that may be used in the present invention is the NTAG 210µ family of tags manufactured/marketed by NXP Semiconductors of The Netherlands. Another non-limiting commercial example of a near field communication (NFC) tag chip, which includes a microcontroller, that may be used in the present invention is the ST25T family of tags manufactured/marketed by ST Microelectronics of Switzerland. Another non-limiting commercial example of a near field communication (NFC) tag chip, which includes an analog front end (AFE), that may be used in the present invention is the ST25R3916/7 manufactured/marketed by ST Microelectronics of Switzerland.

The analog front end (AFE) 52 is used to drive the electrochemistry and sample the results. In one embodiment, the analog front end 52 applies voltage to the reagent area 28 that starts the electrochemical reaction between the reagent and the analyte in the fluid sample. The resulting current produced from the electrochemical reaction in this embodiment is sampled by the analog front end 52. This measured value of the current is wirelessly transmitted to the NFC-enabled reader for further processing.

In one embodiment, the analog front end is powered via the NFC-enabled reader such as shown in the NFC tag chip 50 in FIG. 2A. In another embodiment, the AFE is powered by a battery located on the NFC tag chip 150 as shown in FIG. 2B. A non-limiting commercial example of an analog front end (AFE) that may be used in the present invention is AFE4400 manufactured/marketed by Texas Instruments of the USA.

The memory 56 of the NFC tag chip 50 is typically in the form of an EEPROM. One non-limiting example of memory that may be used is 8 kbit EEPROM. It is contemplated that other forms of EEPROM or other types of memory may be used. For example, flash memory may be used in the NFC tag chip.

The microcontroller 60 in the electrochemical test sensor 10 executes operations involved with receiving and sending signals through the antenna 68 to the NFC-enabled reader. The microcontroller 60 assists in controlling the analog front end (AFE) 52 and converting electrical signals to readable data. The microcontroller 60 directs the analog front end (AFE) 52 to start sampling. A non-limiting commercial example of a microcontroller that may be used in the present invention is the LPC800 series manufactured/marketed by NXP Semiconductors of the Netherlands.

It is contemplated that the analog front end (AFE), microcontroller and near field communicator (NFC) may be separate chips or components. The NFC tag chip in these embodiments would be considered a lower end tag chip. It is contemplated that two or more of these components may be integrated together. In one non-limiting example, the analog front end (AFE) and near field communicator (NFC) are integrated together. In another example, the microcontroller and the near field communicator (NFC) are integrated together. In a further example, the analog front end (AFE) and microcontroller are integrated together. It is contemplated that the analog front end (AFE), microcontroller and near field communicator (NFC) may all be integrated together such as shown with the NFC chip tag 50 in FIG. 2A.

In one embodiment, a system for determining analyte information (e.g., analyte concentration) includes an electrochemical test sensor and an NFC-enabled reader. The NFC-enabled reader is configured to wirelessly receive data from the electrochemical test sensor to assist in determining the analyte concentration of the fluid sample. The electrochemical test sensor is adapted to receive a fluid sample including an analyte. The electrochemical test sensor comprises a base. The base includes an enzyme adapted to react with the analyte. The electrochemical test sensor further including a plurality of electrodes, a near field communication (NFC) tag chip, an analog front end (AFE) and a microcontroller. One non-limiting example of an electrochemical test sensor that may be used is the electrochemical test sensor 10.

Figure 4:
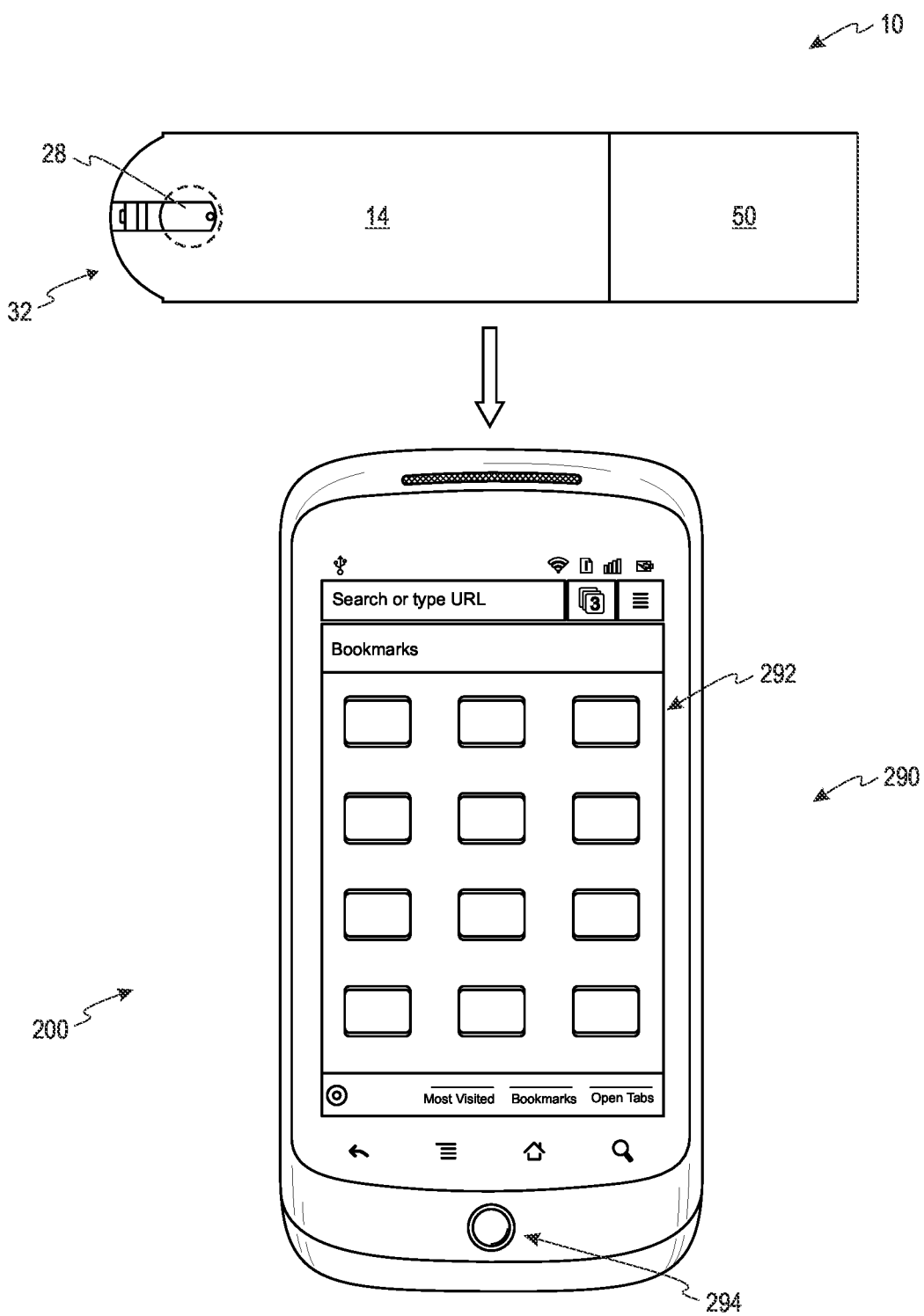
FIG. 4 is a system including the electrochemical test sensor of FIGS. 1A and 1C and an NFC-enabled reader according to one embodiment.

Referring to FIG. 4, a system 200 includes the electrochemical test sensor 10 and an NFC-enabled reader 290. NFC-enabled readers can read NFC chip tags on the electrochemical test sensor to get information therefrom. The NFC-enabled reader typically may be a smartphone, tablet or computer. It is also contemplated that other NFC-enabled readers may be used. For example, the NFC-enabled reader may be a kiosk. The kiosk may be a kiosk specifically designed for use in determining an analyte concentration of a fluid sample. The kiosk may be useful in health care settings such as a hospital.

The NFC-enabled reader 290 includes a display 292 and one or more buttons 294 or other mechanism for navigating the display 292. The display 292 is typically used to show analyte information or other information of the fluid sample. The display 292 may be analog or digital. The display 292 may be a LCD, a LED, an OLED, a vacuum fluorescent, or other display adapted to show numerical readings such as analyte information. It is contemplated that the analyte information (e.g., analyte concentration) may be conveyed in an audio communication from the NFC-enabled reader.

To assist in determining analyte information (e.g., analyte concentration), in one embodiment, one or more algorithms are downloaded to the NFC-enabled reader 290. Here, the NFC-enabled reader is shown as a smartphone. As discussed above, the NFC-enabled reader may be a tablet, computer or a kiosk. The NFC-enabled reader using the one or more algorithms will take the raw data from the electrochemical test sensor that is wirelessly transmitted and calculate the analyte information. The one or more algorithms may be downloaded and stored in the NFC-enabled reader.

In another embodiment, the near field communication (NFC) tag chip may include and transmit read-only data. This read-only data identifies the electrochemical test sensor to the NFC-enabled reader. The reader recognizes the read-only data and runs the proper one or more algorithms to determine the analyte information (e.g., analyte concentration).

In a further embodiment, the NFC-enabled reader may include log-in information for a user before using the algorithm to assist in collecting and categorizing the data. The data may be stored locally in the NFC-enabled reader or may be sent externally to another storage location, such as a cloud-based storage location. It is contemplated that the data may be sent to other locations.

Figure 5:
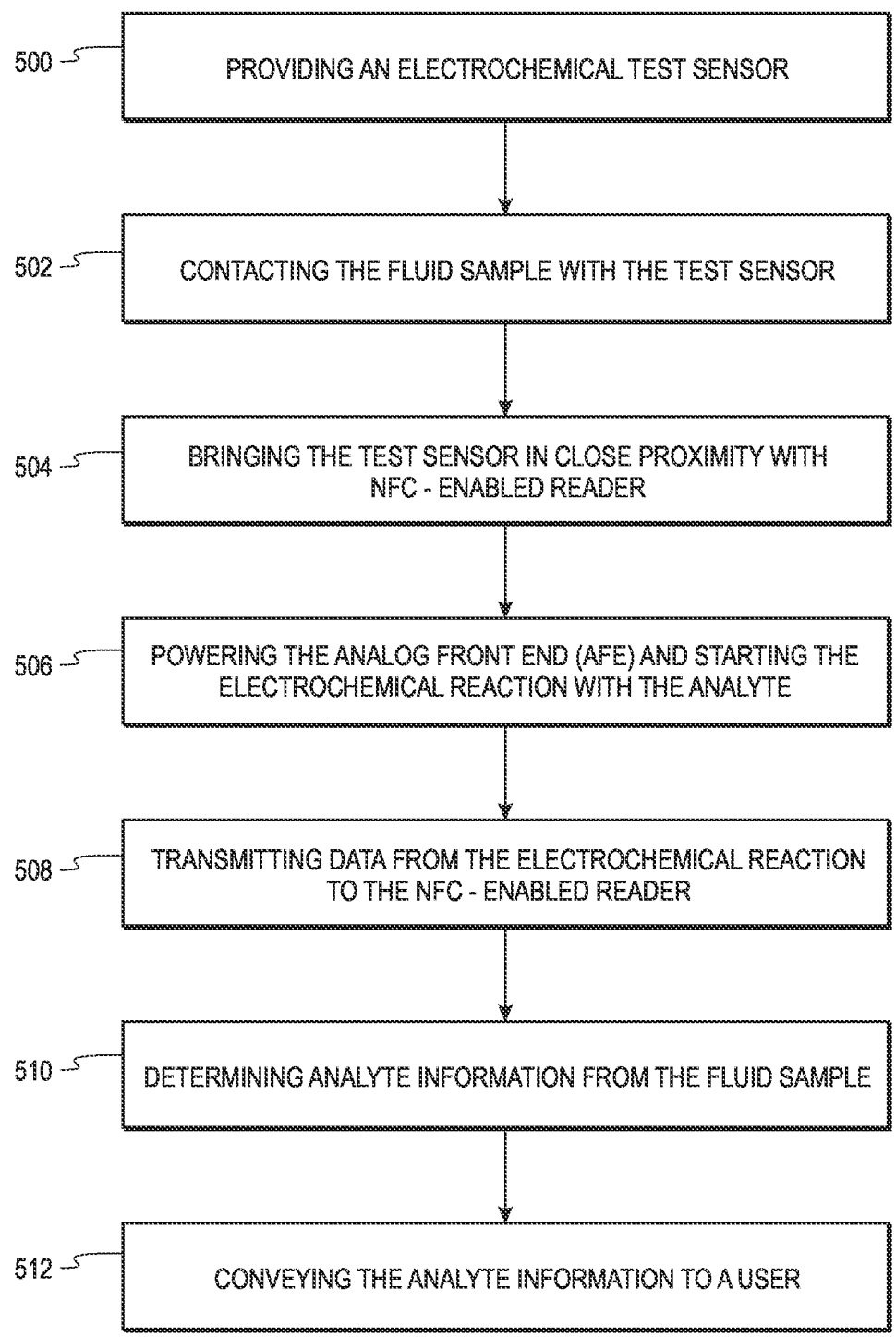
FIG. 5 is a flow chart of steps to determine analyte information according to one method.

One method is shown in the flowchart of FIG. 5 and includes steps for determining and conveying analyte information to a user. Referring to FIG. 5, step 500 provides an electrochemical test sensor. In step 502, the fluid sample contacts the electrochemical test sensor. Step 504 brings the electrochemical test sensor in close proximity with an NFC-enabled reader. Step 506 powers the analog front end (AFE) and starts the electrochemical reaction with the analyte. In step 508, data is transmitted from the electrochemical reaction to the NFC-enabled reader. In step 510, analyte information (e.g., analyte concentration) is determined from the fluid sample. In step 512, the analyte information is conveyed to a user.

In one method, the analyte information of a fluid sample is determined. An electrochemical test sensor is provided. For example, the electrochemical test sensor that may be used is the electrochemical test sensor 10. The fluid sample contacts the reagent area 28 via the fluid-receiving area 16. In one method, the fluid sample is obtained by pricking a finger. In this case, the fluid sample is blood. The fluid sample may be obtained by other methods. It is contemplated that other fluids may be used.

The electrochemical test sensor is brought or placed in close proximity to an NFC-enabled reader. After bringing the electrochemical test sensor in close proximity to the NFC-enabled reader, the near field communication (NFC) tag chip 50, including the analog front end (AFE) 52 is powered. In one non-limiting example, a tap of an NFC-enabled device to the electrochemical test sensor can be used to instantly share the analyte information of the electrochemical test sensor. Tapping an NFC-enabled reader or device to the electrochemical test sensor can be used to establish a wireless connection between the two devices.

In another example, the electrochemical test sensor can be in close proximity as the above discussed distances. NFC is currently used for communication distances of about 20 cm or less, and more likely about 10 cm or less. In other embodiments, the NFC is typically used in communication distances of less than about 8 cm or less than 6 cm. In another embodiment, the NFC is more commonly used in communication distances of less than about 5 or about less than about 4 cm. The NFC of the electrochemical test sensor wirelessly communicates with the NFC-enabled reader when in close proximity.

The analog front end 52 assists in starting an electrochemical reaction with the analyte after receiving instructions from the microprocessor 60. After the reaction has started, data from the electrochemical reaction via the NFC tag chip of the electrochemical test sensor is wirelessly transmitted to the NFC-enabled reader. The analyte information of the fluid sample is determined on the NFC-enabled reader using the data received from the electrochemical test sensor and at least one algorithm. The algorithm may be stored on NFC-enabled reader or in server farms in the cloud.

In one method, the analog front end (AFE) assists in starting the electrochemical reaction with the analyte by providing at least one voltage to the fluid sample resulting in current formed from the electrochemical reaction. The analog front end may provide an excitation signal to start the electrochemical reaction. During electrochemical analyses, an excitation signal is applied to the sample of the biological fluid. The excitation signal may be a potential or current and may be constant, variable, or a combination thereof. The excitation signal may be applied as a single pulse or in multiple pulses, sequences, or cycles. Various electrochemical processes may be used such as amperometry, coulometry, voltammetry, gated amperometry, gated voltammetry, and the like.

In one method, the near field communication (NFC) tag chip 50 is powered by the NFC-enabled reader. The NFC-enabled reader may be the NFC-enabled readers discussed above, including the NFC-enabled reader 290. In another method, as discussed with respect to FIG. 2B, the battery 84 powers the NFC tag chip 150 and/or the AFE module 52 for signal sampling.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

What is claimed is:

1. An electrochemical test sensor for receiving a fluid sample including an analyte, the electrochemical test sensor comprising:
    a base comprising:
        an enzyme adapted to react with the analyte;
        a counter electrode connected to a first conductive lead;
        a working electrode connected to a second conductive lead;
        a detection fill electrode connected to a third conductive lead;
        a hematocrit electrode connected to a fourth conductive lead;
    a lid;
    a spacer disposed between the base and the lid,
    wherein the base, the lid, and the spacer form a channel for receiving the fluid sample;
    a near field communication (NFC) tag chip, the NFC tag chip comprising a battery;
    an analog front end (AFE), the AFE electrically connected to each of the first conductive lead, the second conductive lead, the third conductive lead, and the fourth conductive lead; and
    a microcontroller.

2. The electrochemical test sensor of claim 1, wherein the channel is a capillary channel.

3. The electrochemical test sensor of claim 1, wherein the enzyme is glucose dehydrogenase or glucose oxidase.

4. The electrochemical test sensor of claim 1, wherein the analog front end (AFE) is integrated into the near field communication (NFC) tag chip.

5. The electrochemical test sensor of claim 1, wherein the microcontroller is integrated into the near field communication (NFC) tag chip.

6. The electrochemical test sensor of claim 1, wherein the analog front end (AFE) and the microcontroller are integrated into the near field communication (NFC) tag chip.

7. The electrochemical test sensor of claim 1, wherein the electrochemical test sensor further includes a mediator.

8. The electrochemical test sensor of claim 1, wherein the electrochemical test sensor is configured for peer-to-peer communication with an NFC reader.

9. A system for determining analyte information of a fluid sample, the system comprising:
    an electrochemical test sensor adapted to receive the fluid sample of an analyte, the electrochemical test sensor comprising:
        a base comprising:
            an enzyme adapted to react with the analyte;
            a counter electrode connected to a first conductive lead;
            a working electrode connected to a second conductive lead;
            a detection fill electrode connected to a third conductive lead; and
            a hematocrit electrode connected to a fourth conductive lead;
        a lid;
        a spacer disposed between the base and the lid,
        wherein the base, the lid, and the spacer form a channel for receiving the fluid sample;
        a near field communication (NFC) tag chip, the NFC tag chip comprising a battery;
        an analog front end (AFE); and
        a microcontroller; and
    an NFC-enabled reader configured to wirelessly receive data from the electrochemical test sensor to assist in determining the analyte information of the fluid sample.

10. The system of claim 9, wherein the NFC-enabled reader is a smartphone, a tablet, or a computer.

11. The system of claim 9, wherein the NFC-enabled reader is a kiosk.

12. The system of claim 9, wherein the NFC-enabled reader displays the analyte information of the fluid sample.

13. The system of claim 9, wherein the NFC tag chip is adapted to include and transmit read-only data, wherein the read-only data identifies the electrochemical test sensor to the NFC-enabled reader to assist in determining analyte information of the fluid sample.

14. The system of claim 9, wherein the NFC-enabled reader includes log-in information.

15. The system of claim 9, wherein the analog front end (AFE) and the microcontroller are integrated into the near field communication (NFC) tag chip.

16. The system of claim 9, wherein the electrochemical test sensor further includes a mediator.

17. The system of claim 9, wherein the electrochemical test sensor is configured for peer-to-peer communication with the NFC-enabled reader.

18. A method for determining analyte information of a fluid sample, the method comprising:
    providing an electrochemical test sensor adapted to receive the fluid sample of an analyte, the electrochemical test sensor comprising:
        a base comprising:
            an enzyme adapted to react with the analyte;
            a counter electrode connected to a first conductive lead;
            a working electrode connected to a second conductive lead;
            a detection fill electrode connected to a third conductive lead;
            a hematocrit electrode connected to a fourth conductive lead;
        a lid;
        a spacer disposed between the base and the lid,
        wherein the base, the lid, and the spacer form a channel for receiving the fluid sample;
        a near field communication (NFC) tag chip, the NFC tag chip comprising a battery;
        an analog front end (AFE); and
        a microcontroller;
    when the electrochemical test sensor is in proximity to an NFC-enabled reader, powering the near field communication (NFC) tag chip and the analog front end (AFE),
    wherein the analog front end is configured to assist in starting an electrochemical reaction with the analyte and the fluid sample, wherein the fluid sample is in contact with the electrochemical test sensor;

wirelessly transmitting data from the electrochemical reaction via the NFC tag chip of the electrochemical test sensor to the NFC-enabled reader; and determining the analyte information of the fluid sample on the NFC-enabled reader using the data received from the electrochemical test sensor.

19. The method of claim 18, wherein the fluid sample is blood.

20. The method of claim 18, wherein the NFC-enabled reader is a smartphone, a tablet, or a computer.

21. The method of claim 18, wherein the NFC-enabled reader is a kiosk.

22. The method of claim 18, wherein a distance between the electrochemical test sensor and the NFC-enabled reader is less than 10 cm.

23. The method of claim 22, wherein the distance between the electrochemical test sensor and the NFC-enabled reader is less than 6 cm.

24. The method of claim 18, wherein the analyte information of the fluid sample is an analyte concentration.

25. The method of claim 18, wherein the analog front end assists in starting the electrochemical reaction with the analyte by providing at least one voltage to the fluid sample resulting in currents formed from the electrochemical reaction with the analyte.

26. The method of claim 18, wherein the NFC-enabled reader uses a stored algorithm and the data received from the electrochemical test sensor to determine the analyte information of the fluid sample.

27. The method of claim 18, wherein the NFC-enabled reader uses an algorithm from a server farm in a cloud-based storage location and the data received from the electrochemical test sensor to determine the analyte information of the fluid sample.

28. The method of claim 18, wherein the analyte information of the fluid sample is conveyed to a user via a display or conveyed to the user in an audio communication.

* * * * *